United States Patent
McLeod et al.

(10) Patent No.: US 12,285,288 B2
(45) Date of Patent: Apr. 29, 2025

(54) SYSTEMS AND METHODS FOR DETECTING TISSUE CONTACT BY AN ULTRASOUND PROBE

(71) Applicant: Intuitive Surgical Operations, Inc., Sunnyvale, CA (US)

(72) Inventors: A. Jonathan McLeod, Sunnyvale, CA (US); Mahdi Azizian, San Jose, CA (US); Daniel Proksch, San Jose, CA (US); Azad Shademan, Campbell, CA (US); Pourya Shirazian, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 374 days.

(21) Appl. No.: 17/611,602

(22) PCT Filed: May 29, 2020

(86) PCT No.: PCT/US2020/035217
§ 371 (c)(1),
(2) Date: Nov. 16, 2021

(87) PCT Pub. No.: WO2020/243493
PCT Pub. Date: Dec. 3, 2020

(65) Prior Publication Data
US 2022/0175346 A1 Jun. 9, 2022

Related U.S. Application Data

(60) Provisional application No. 62/855,881, filed on May 31, 2019.

(51) Int. Cl.
*A61B 8/00* (2006.01)
*A61B 8/12* (2006.01)

(52) U.S. Cl.
CPC ............... *A61B 8/429* (2013.01); *A61B 8/12* (2013.01); *A61B 8/5207* (2013.01); *A61B 8/54* (2013.01)

(58) Field of Classification Search
CPC ......... A61B 8/429; A61B 8/12; A61B 8/5207; A61B 8/54; A61B 8/5269; A61B 8/4281; A61B 8/58
See application file for complete search history.

(56) References Cited

U.S. PATENT DOCUMENTS 9,558,549 B2 * 1/2017 Ishikawa ............. A61B 5/055
10,959,779 B2 * 3/2021 Piron .................. A61B 5/0075
(Continued)

FOREIGN PATENT DOCUMENTS

| CN | 109788944 A | 5/2019 |
|---|---|---|
| EP | 3298967 A1 | 3/2018 |

(Continued)

OTHER PUBLICATIONS

Pazinato et. al., "Pixel-Level Tissue Classification for Ultrasound Images"; IEEE Journal of Biomedical and Health Informatics, vol. 20, No. 1, Jan. 2016 (Year: 2016).*

(Continued)

*Primary Examiner* — Keith M Raymond
*Assistant Examiner* — Fikirte (Fiki) T Ashine

(57) ABSTRACT

A contact detection system is configured to classify each pixel in a plurality of pixels included in an ultrasound image captured by an ultrasound probe located within a patient as either showing tissue or showing non-tissue; determine an average pixel classification representative of a number of pixels classified as showing tissue compared to a number of pixels classified as showing non-tissue; determine, if the average pixel classification is above a first contact state threshold, that the ultrasound probe is in a first contact state that indicates that the ultrasound probe is in operative physical contact with the tissue; and determine, if the average pixel classification is below a second contact state threshold lower than the first contact state threshold, that the ultrasound probe is in a second contact state that indicates that the ultrasound probe is not in operative physical contact with the tissue.

18 Claims, 13 Drawing Sheets

(56) References Cited

U.S. PATENT DOCUMENTS

| | | | |
|---|---|---|---|
| 2011/0245652 A1* | 10/2011 | Oishi | G01S 15/8977 |
| | | | 600/407 |
| 2013/0226003 A1* | 8/2013 | Edic | A61B 6/507 |
| | | | 600/504 |
| 2014/0037168 A1* | 2/2014 | Ishikawa | A61B 8/5261 |
| | | | 382/130 |
| 2016/0148373 A1* | 5/2016 | Robinson | G06T 7/70 |
| | | | 382/103 |
| 2016/0358314 A1* | 12/2016 | Ji | G06T 5/50 |
| 2018/0085090 A1* | 3/2018 | Park | A61B 8/5207 |
| 2018/0168546 A1 | 6/2018 | Ebata | |
| 2019/0192121 A1* | 6/2019 | Ebata | A61B 8/4254 |
| 2020/0077976 A1* | 3/2020 | Hirai | A61B 8/58 |

FOREIGN PATENT DOCUMENTS

| | | | |
|---|---|---|---|
| JP | 2006212146 A | | 8/2006 |
| JP | 4253494 B2 | * | 4/2009 |
| JP | 2015231436 A | * | 12/2015 |
| WO | WO-2007030173 A1 | | 3/2007 |
| WO | WO-2016013454 A1 | | 1/2016 |

OTHER PUBLICATIONS

Chen et. al., "Diagnosis of Breast Tumors With Sonographic Texture Analysis Using Wavelet Transform and Neural Networks"; Ultrasound in Med. & Biol., vol. 28, No. 10, pp. 1301-1310, 2002 (Year: 2002).*

International Preliminary Report on Patentability for Application No. PCT/US2020/035217 mailed on Dec. 9, 2021, 13 pages.

International Search Report and Written Opinion for Application No. PCT/US2020/035217, mailed Nov. 16, 2020, 19 pages.

Invitation to pay additional fee received from the International Search Authority for PCT/US202020/035217, mailed Sep. 24, 2020, 11 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR DETECTING TISSUE CONTACT BY AN ULTRASOUND PROBE

RELATED APPLICATIONS

The present application is a U.S. National Stage Application under 35 U.S.C. § 371 of International Application No. PCT/US2020/035217, filed on May 29, 2020, which claims priority to U.S. Provisional Patent Application No. 62/855,881, filed on May 31, 2019, the contents of which are hereby incorporated by reference in their entirety.

BACKGROUND INFORMATION

During a surgical procedure, an endoscope may be positioned within a patient to capture an endoscopic image of a surgical area within the patient. The endoscopic image may be presented to the surgeon by way of a display device so that the surgeon may visualize outer surfaces of internal anatomy and other types of tissue within the patient while performing the surgical procedure.

In some scenarios, an ultrasound probe may also be positioned within the patient to capture an ultrasound image within the patient during the surgical procedure. The ultrasound image may be presented concurrently with the endoscopic image to the surgeon (e.g., by way of the same display device that displays the endoscopic image). In this manner, the surgeon may visualize both the outer surfaces of the tissue included in the surgical area (using the endoscopic image) and structures internal to the tissue in the surgical area (using the ultrasound image) while performing the surgical procedure.

To capture a useful ultrasound image, the ultrasound probe must make good physical contact with tissue. Poor tissue contact by the ultrasound probe will result in an ultrasound image dominated by noise (e.g., noise generated by electronic components and/or signal artifacts that occur near the transducer surface of the ultrasound probe). If the ultrasound probe is not making good tissue contact, it may be distracting and/or useless to present the ultrasound image to the surgeon during the surgical procedure.

SUMMARY

An exemplary system includes a memory storing instructions; and a processor communicatively coupled to the memory and configured to execute the instructions to classify each pixel in a plurality of pixels included in an ultrasound image captured by an ultrasound probe located within a patient as either showing tissue or showing non-tissue; and determine, based on the classification of each pixel in the plurality of pixels as either showing tissue or showing non-tissue, a contact state of the ultrasound probe, the contact state indicating whether the ultrasound probe is in operative physical contact with tissue of the patient.

Another exemplary system includes a memory storing instructions and a processor communicatively coupled to the memory and configured to execute the instructions to determine, based on an ultrasound image captured by an ultrasound probe located within a patient, a contact state of the ultrasound probe, the contact state indicating whether the ultrasound probe is in operative physical contact with tissue of the patient; and control, based on the contact state of the ultrasound probe, a display of the ultrasound image within a viewable image displayed by a display device.

An exemplary method includes classifying, by a contact detection system, each pixel in a plurality of pixels included in an ultrasound image captured by an ultrasound probe located within a patient as either showing tissue or showing non-tissue; and determining, by the contact detection system based on the classifying of each pixel in the plurality of pixels as either showing tissue or showing non-tissue, a contact state of the ultrasound probe, the contact state indicating whether the ultrasound probe is in operative physical contact with tissue of the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
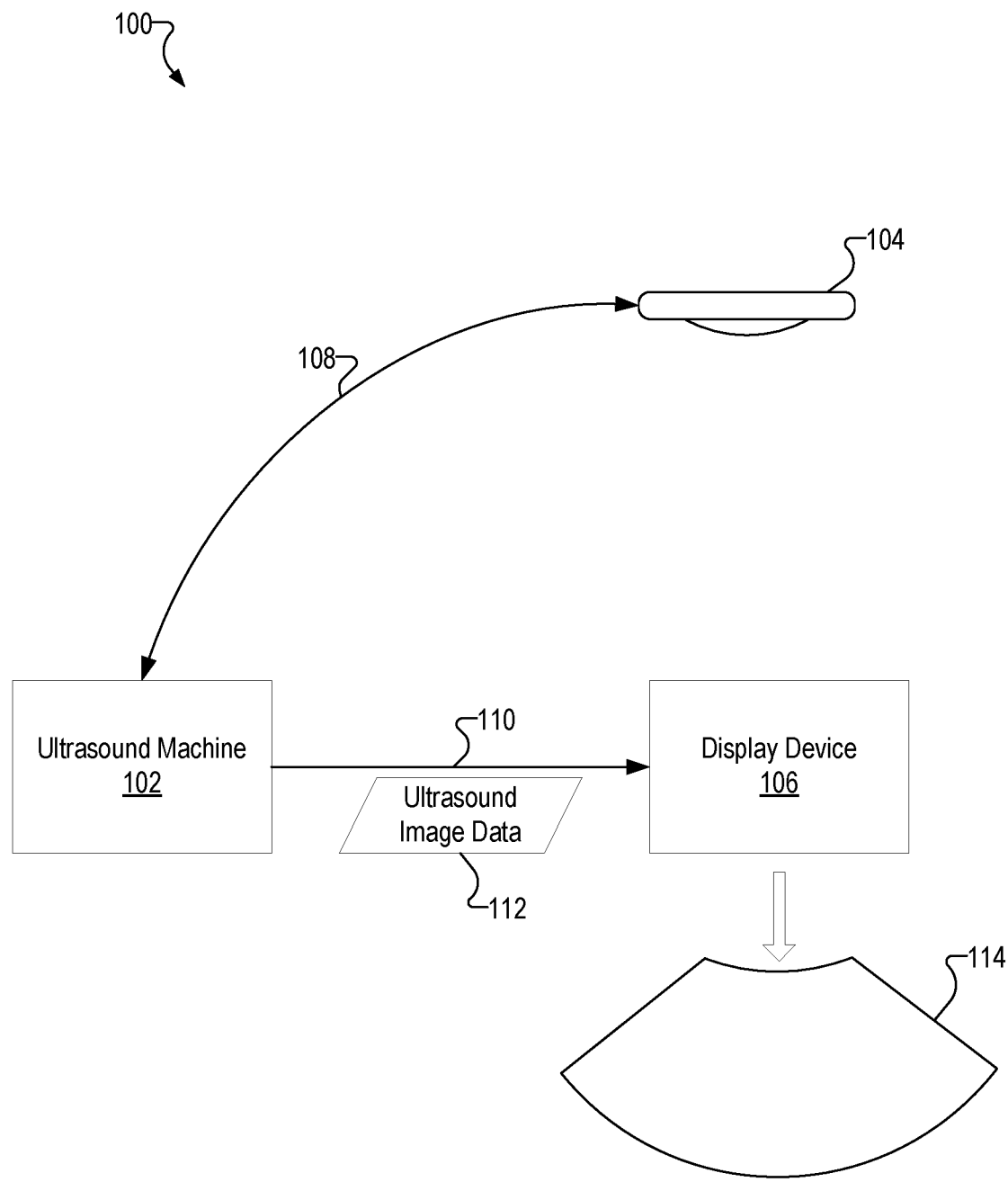
FIG. 1 illustrates various components of an exemplary ultrasound imaging system according to principles described herein.

Systems and methods for detecting tissue contact by an ultrasound probe are described herein. For example, a contact detection system may be configured to classify each pixel in a plurality of pixels included in an ultrasound image captured by an ultrasound probe located within a patient as either showing tissue or showing non-tissue, and determine, based on the classification of each pixel in the plurality of pixels as either showing tissue or showing non-tissue, a contact state of the ultrasound probe. The contact state indicates whether the ultrasound probe is in operative physical contact with tissue of the patient.

In some examples, the contact detection system may determine local descriptor values for a plurality of pixels included in an ultrasound image captured by an ultrasound probe located within a patient and use the local descriptor values to perform the classification. As described herein, the local descriptor values may characterize an intensity distribution and/or a spatial autocorrelation for each pixel in the plurality of pixels.

As used herein, operative physical contact refers to when the ultrasound probe is making sufficient enough tissue contact to capture a useful ultrasound image (i.e., an ultrasound image that includes at least a threshold amount of useful information instead of or in addition to noise, where the threshold amount may be determined in any of the ways described herein). Hence, an ultrasound probe may be in operative physical contact with tissue by being in full physical contact with the tissue or by being in partial physical contact with the tissue, as long as the partial physical contact is sufficient to render a useful ultrasound image. The ultrasound probe is not in operative physical contact with tissue when the ultrasound probe is not making sufficient enough tissue contact to capture a useful ultrasound image.

Based on the determined contact state of the ultrasound probe, the contact detection system may perform one or more operations. For example, based on the contact state of the ultrasound probe, the contact detection system may control a display of the ultrasound image within a viewable image displayed by a display device, set a parameter of an ultrasound machine connected to the ultrasound probe, and/or generate a control signal configured to be used by a computer-assisted surgical system to control a positioning of the ultrasound probe. These and other operations that may be performed by the contact detection system based on the determined contact state of the ultrasound probe are described herein.

The systems and methods described herein may provide various advantages and benefits. For example, the systems and methods described herein may intelligently prevent an ultrasound image from being included in a viewable image presented to a user (e.g., a surgeon) when the ultrasound image does not include useful information, thereby providing an improved visual experience for the user during a surgical procedure. Additionally or alternatively, the systems and methods described herein may automatically optimize one or more settings of an ultrasound machine used during a surgical procedure, thereby improving a quality of an ultrasound image generated by the ultrasound machine. Additionally or alternatively, the systems and methods described herein may facilitate optimal positioning of an ultrasound probe within a patient. Each of these operations may improve efficiency and effectiveness of a surgical procedure.

The systems and methods described herein advantageously determine whether an ultrasound probe is in operative physical contact with tissue based solely on the contents of an ultrasound image (also referred to as a B-mode image). In particular, the systems and methods described herein may be configured to distinguish between speckle (content in an ultrasound image that results from constructive and destructive interference of sound waves reflecting off of structures within the tissue) and non-useful noise included in the ultrasound image. Although speckle may visually appear similar to noise, the intensity distribution and spatial autocorrelation of speckle within an ultrasound image differs from noise. The systems and methods leverage this distinction to determine whether an ultrasound probe is in operative physical contact with tissue. This may advantageously result in substantially real-time determination of the contact state of the ultrasound probe.

These and other advantages and benefits of the systems and methods described herein will be made apparent herein.

FIG. 1 illustrates various components of an exemplary ultrasound imaging system 100. As shown, ultrasound imaging system 100 may include an ultrasound machine 102, an ultrasound probe 104, and a display device 106. Ultrasound machine 102 is communicatively coupled to ultrasound probe 104 by way of communication link 108 and to display device 106 by way of communication link 110. Communication links 108 and 110 may be implemented by any suitable wired and/or wireless components. For example, communication link 108 may be implemented a cable, shaft, or other structure that carries one or more wires that communicatively interconnect ultrasound machine 102 and ultrasound probe 104.

Ultrasound machine 102 may include computing components configured to facilitate generation of an ultrasound image. For example, ultrasound machine 102 may include a controller configured to control operation of ultrasound probe 104 by directing ultrasound probe 104 to emit and detect sound waves. In some examples, the controller and/or any other component of ultrasound machine 102 is configured to operate in accordance with one or more definable (e.g., adjustable) parameters. For example, ultrasound machine 102 may be configured to direct ultrasound probe 104 to emit sound waves having a definable frequency and/or receive sound waves at a particular gain. As another example, ultrasound machine 102 may also be configured to specify a fan depth of ultrasound image 114.

Ultrasound machine 102 may additionally or alternatively include one or more image processing components configured to generate ultrasound image data 112 based on sound waves detected by ultrasound probe 104. As shown, ultrasound machine 102 may transmit ultrasound image data 112 to display device 106 by way of communication link 110. Display device 106 may use ultrasound image data 112 to generate and display an ultrasound image 114.

In some examples, ultrasound machine 102 is connected to, integrated into, or implemented by a surgical system. For example, ultrasound machine 102 may be connected to, integrated into, or implemented by a computer-assisted surgical system that utilizes robotic and/or teleoperation technology to perform a surgical procedure (e.g., a minimally invasive surgical procedure). An exemplary computer-assisted surgical system is described herein.

Ultrasound probe 104 (also called a transducer) is configured to capture an ultrasound image by emitting sound waves and detecting the sound waves after they reflect from structures inside a body (e.g., structures internal to an organ or other tissue within a patient). Ultrasound probe 104 may have any suitable shape and/or size as may serve a particular implementation. In some examples, ultrasound probe 104 may have a shape and size that allow ultrasound probe 104 to be inserted into a patient by way of a port in a body wall of the patient. In these examples, a position of ultrasound probe 104 within the patient may be controlled manually (e.g., by manually manipulating a shaft to which ultrasound probe 104 is connected). Additionally or alternatively, the position of ultrasound probe 104 may be controlled in a computer-assisted manner (e.g., by a computer-assisted surgical system that utilizes robotic and/or teleoperation technology).

Display device 106 may be implemented by any suitable device configured to render or display ultrasound image 114 based on ultrasound image data 112. As described herein, display device 106 may also be configured to display additional or alternative images and/or information. For example, in some scenarios, display device 106 may display a viewable image that includes ultrasound image 114 together with an endoscopic image acquired by an endoscope and/or a pre-operative model (e.g., a 3D model) of patient anatomy registered with the endoscopic image.

Figure 2A:
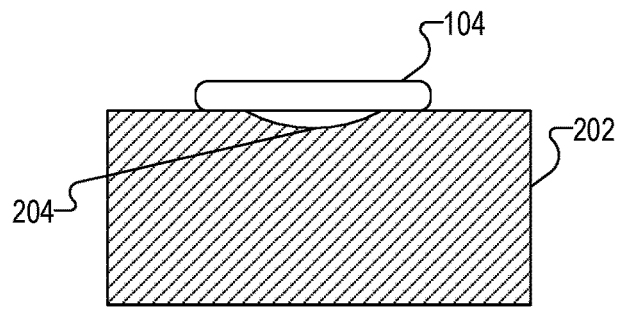
FIGS. 2A-2C illustrate different possible contact states of an ultrasound probe with respect to tissue according to principles described herein.
Figure 2B:
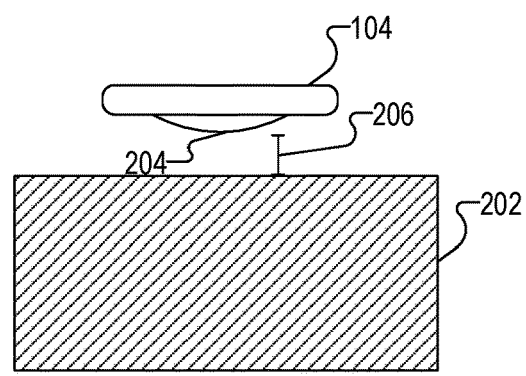
Figure 2C:
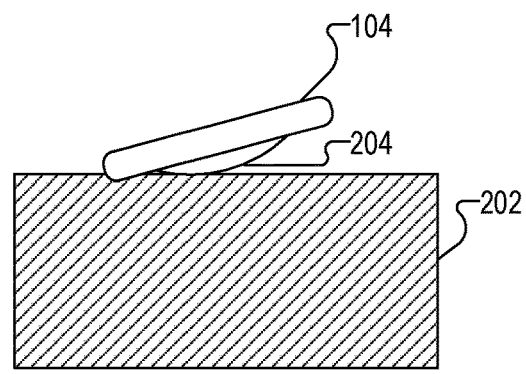

As mentioned, ultrasound probe 104 must be in operative physical contact with tissue of the patient to capture a useful ultrasound image. To illustrate, FIGS. 2A-2C illustrate different possible contact states of ultrasound probe 104 with respect to tissue 202. Tissue 202 may represent any organ or anatomical feature of a patient.

FIG. 2A illustrates a first contact state in which ultrasound probe 104 is in operative physical contact with tissue 202. As shown, an entire bottom surface 204 (which is convex-shaped in the examples provided herein) of ultrasound probe 104 is in physical contact with tissue 202. In this contact state, there is sufficient acoustic coupling between ultrasound probe 104 and tissue 202 to capture a useful ultrasound image.

FIG. 2B illustrates a second contact state in which ultrasound probe 104 is not in operative physical contact with tissue 202. As shown, bottom surface 204 of ultrasound probe 104 is separated from tissue 202 by a gap 206. In this contact state, because there is no physical contact between ultrasound probe 104 and tissue 202, an ultrasound image captured by ultrasound probe 104 will be dominated by noise, and is therefore not useful to a user.

FIG. 2C illustrates another instance of the second contact state in which ultrasound probe 104 is not in operative physical contact with tissue 202. In FIG. 2C, only a small portion of bottom surface 204 of ultrasound probe 104 is in physical contact with tissue 202. Because of this, ultrasound probe 104 may be determined to not be in operative physical contact with tissue 202 if the amount of useful information included in an ultrasound image generated by ultrasound probe 104 is below a particular threshold. Hence, as shown in FIG. 2C, ultrasound probe 104 may sometimes not be in operative physical contact with tissue 202 even though ultrasound probe 104 is at least partially touching tissue 202.

Figure 3:
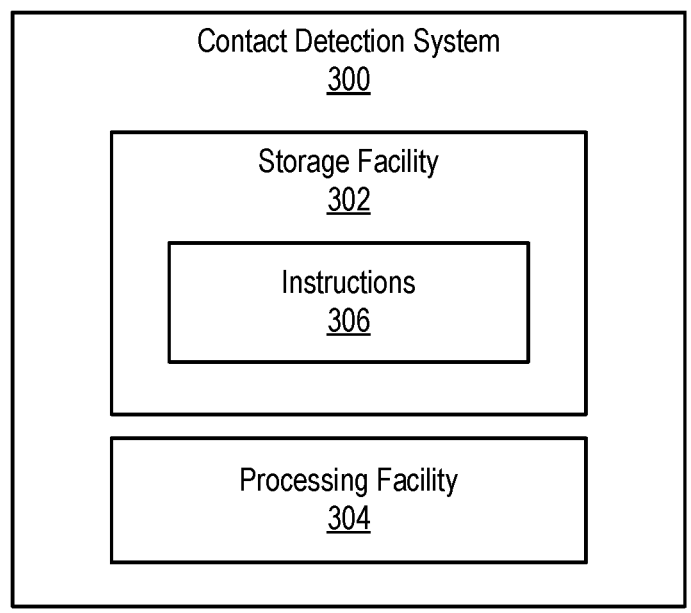
FIG. 3 illustrates an exemplary contact detection system according to principles described herein.

FIG. 3 illustrates an exemplary contact detection system 300 ("system 300") that may be configured to detect tissue contact by an ultrasound probe (e.g., ultrasound probe 104). System 300 may be included in, implemented by, or connected to any of surgical systems, ultrasound machines, or other computing systems described herein. For example, system 300 may be implemented by a computer-assisted surgical system and/or ultrasound machine 102. As another example, contact detection system 300 may be implemented by a stand-alone computing system communicatively coupled to a computer-assisted surgical system and/or ultrasound machine 102.

As shown, system 300 may include, without limitation, a storage facility 302 and a processing facility 304 selectively and communicatively coupled to one another. Facilities 302 and 304 may each include or be implemented by hardware and/or software components (e.g., processors, memories, communication interfaces, instructions stored in memory for execution by the processors, etc.). For example, facilities 302 and 304 may be implemented by any component in a computer-assisted surgical system. In some examples, facilities 302 and 304 may be distributed between multiple devices and/or multiple locations as may serve a particular implementation.

Storage facility 302 may maintain (e.g., store) executable data used by processing facility 304 to perform any of the operations described herein. For example, storage facility 302 may store instructions 306 that may be executed by processing facility 304 to perform any of the operations described herein. Instructions 306 may be implemented by any suitable application, software, code, and/or other executable data instance. Storage facility 302 may also maintain any data received, generated, managed, used, and/or transmitted by processing facility 304.

Processing facility 304 may be configured to perform (e.g., execute instructions 306 stored in storage facility 302 to perform) various operations associated with detecting tissue contact by an ultrasound probe. For example, processing facility 304 may be configured to classify each pixel in a plurality of pixels included in an ultrasound image captured by an ultrasound probe located within a patient as either showing tissue or showing non-tissue. Processing facility 304 may be further configured to determine, based on the classification of each pixel in the plurality of pixels as either showing tissue or showing non-tissue, a contact state of the ultrasound probe. These and other operations that may be performed by processing facility 304 are described herein. In the description that follows, any references to operations performed by system 300 may be understood to be performed by processing facility 304 of system 300.

Figure 4A:
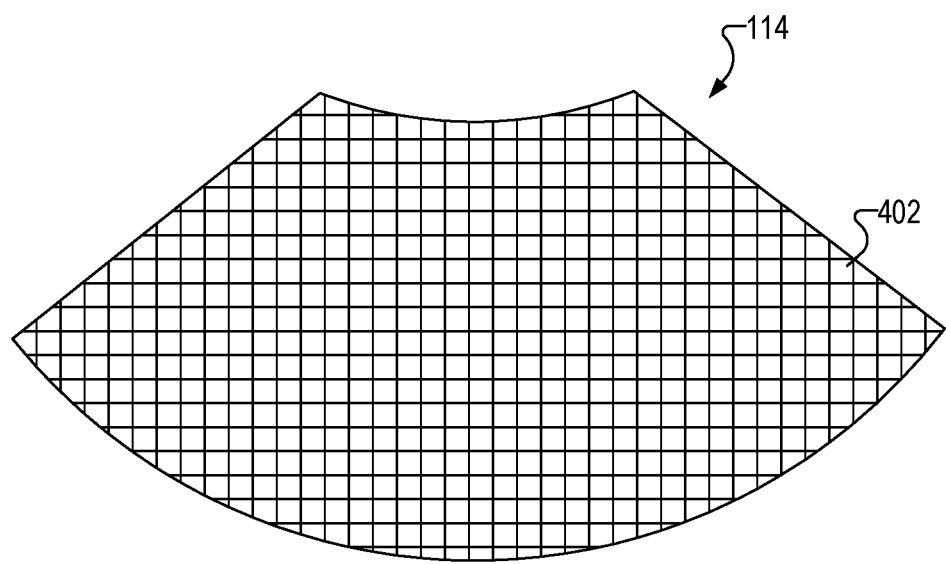
FIG. 4A illustrates a detailed view of an ultrasound image according to principles described herein.

FIG. 4A illustrates a detailed view of ultrasound image 114. As shown, ultrasound image 114 includes a plurality of pixels (e.g., pixel 402). Each pixel has an intensity value defined by ultrasound image data 112. The term "pixel" is used herein to refer to any suitably sized and/or shaped region of ultrasound image 114 as may serve a particular implementation.

Figure 4B:
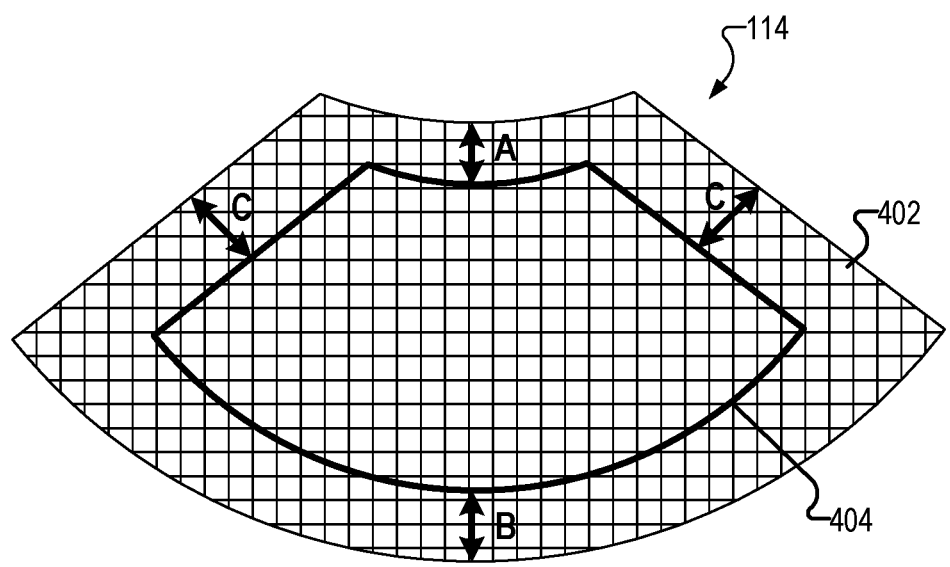
FIG. 4B shows an exemplary region of interest within the ultrasound image of FIG. 4A according to principles described herein.

In some examples, system 300 may limit its processing of pixels for purposes of determining a contact state of ultrasound probe 104 to pixels within a particular region of interest. For example, FIG. 4B shows an exemplary region of interest 404 within ultrasound image 114. In this case, system 300 may only determine local descriptor values for pixels within region of interest 404 and not for a set of pixels outside of region of interest 404. This may limit the impact of artifacts near the ultrasound probe surface (region A in FIG. 4B) and signal dropout deeper in ultrasound image 114 (region B in FIG. 4B) since both of these regions can confound the results of the local descriptor value processing by system 300. As shown, the left and right border regions of ultrasound image 114 (region C in FIG. 4B) may also be excluded from region of interest 404. Alternatively, a border handling heuristic may be used to include border region pixels in the processing. Region of interest 404 may include any suitable number of pixels as may serve a particular implementation. In some examples, region of interest 404 includes all pixels included in ultrasound image 114. In other examples, there may be multiple regions of interest included in ultrasound image 114.

System 300 may determine one or more local descriptor values for each pixel included in region of interest 404 in any suitable manner. The local descriptor values characterize an intensity distribution for each pixel in region of interest 404 and/or a spatial autocorrelation for each pixel in region of interest 404. Exemplary local descriptor values that characterize intensity distribution for a pixel include a moment (e.g., a local variance and/or a mean) of the intensity distribution for the pixel and/or any other metric representative of the intensity distribution for the pixel. Exemplary local descriptor values that characterize spatial autocorrelation include autocorrelation values (e.g., one or more terms of an autocovariance function) and/or any other metric representative of spatial autocorrelation for the pixel.

In some examples, the autocorrelation values determined by system 300 are spatial autocorrelation values (e.g., lag-1 autocorrelation values in either the vertical (y) or horizontal (x) directions). Additionally or alternatively, the autocorrelation values may be temporal. In the examples provided herein, it will be assumed that the autocorrelation values are spatial.

In some examples, system 300 may determine multiple local descriptor values for each pixel in region of interest 404. For example, system 300 may determine both a local variance value and an autocorrelation value for each pixel included in region of interest 404. In some alternative examples, system 300 may determine only a single local descriptor value for each pixel. For example, system 300 may determine only a local variance value for each pixel included in region of interest 404. Examples of determining local descriptor values for pixels are described herein.

System 300 may classify, based on the local descriptor values, pixels as either showing tissue or showing non-tissue in any suitable manner. System 300 may alternatively classify pixels as either showing tissue or showing non-tissue in any other suitable manner. For example, one or more image processing techniques, machine learning techniques, etc. may be used to classify pixels as either showing tissue or showing non-tissue. However, for illustrative purposes, the classification examples herein are based on local descriptor values.

For example, system 300 may compare the local descriptor values to one or more thresholds. To illustrate, system 300 may classify pixels that have local descriptor values above a local descriptor threshold as showing tissue and pixels that have local descriptor values below the local descriptor threshold as showing non-tissue.

As an example, the local descriptors determined by system 300 may include local variance values and autocorrelation values. In this example, system 300 may classify pixels that have local variance values above a variance threshold and autocorrelation values above an autocorrelation threshold as showing tissue. Likewise, system 300 may classify pixels that have local variance values below the variance threshold and/or autocorrelation values below the autocorrelation threshold as showing non-tissue. These thresholds may be determined in a number of different ways, some of which are described herein.

As another example, system 300 may determine only local variance values for each pixel. In this example, system 300 may classify pixels that have local variance values above the variance threshold as showing tissue and pixels that have local variance values below the variance threshold as showing non-tissue.

Additionally or alternatively, system 300 may classify pixels as either showing tissue or showing non-tissue by providing the local descriptor values as inputs into a machine learning model and classifying, based on an output of the machine learning model, each pixel in region of interest 404 as either showing tissue or showing non-tissue. The machine learning model may be supervised and/or unsupervised, and may be implemented by any suitable algorithm, such as logistic regression, classification and regression trees, random forests, and/or neural nets.

Additionally or alternatively, system 300 may classify pixels as either showing tissue or showing non-tissue by evaluating any other type of function as may serve a particular implementation. The function may output a binary classification of showing tissue or non-tissue or a fuzzy value indicating a probability of a pixel as showing either tissue or non-tissue. In the latter case, the probability may then be compared to a threshold to make a binary classification of showing tissue or non-tissue.

Once the pixels in region of interest 404 are classified as either showing tissue or showing non-tissue, system 300 may determine, based on the classification of each pixel as either showing tissue or showing non-tissue, a contact state of the ultrasound probe. The contact state indicates whether the ultrasound probe is in operative physical contact with tissue of the patient.

System 300 may use the classification of each pixel as either showing tissue or showing non-tissue to determine the contact state in any suitable manner. For example, system 300 may determine an average pixel classification representative of a number of pixels classified as showing tissue compared to a number of pixels classified as showing non-tissue. The average pixel classification may be a ratio of pixels classified as showing tissue to pixels classified as showing non-tissue and compare the ratio to a contact state threshold, which may be determined in a number of different ways as described herein. Additionally or alternatively, the average pixel classification could be a mean, median, or other suitable metric.

If the average pixel classification is above the contact state threshold, system 300 may determine that ultrasound probe 104 is in a first contact state that indicates that ultrasound probe 104 is in operative physical contact with the tissue of the patient. If the average pixel classification is below the contact state threshold, system 300 may determine that ultrasound probe 104 is in a second contact state that indicates that ultrasound probe 104 is not in operative physical contact with the tissue of the patient.

In some examples, two different contact state thresholds may be used by system 300 for debouncing purposes. For example, system 100 may initially compare the average pixel classification to a first contact state threshold. Once the average pixel classification goes above the first contact state threshold, system 300 may determine that ultrasound probe 104 is in the first contact state that indicates that ultrasound probe 104 is in operative physical contact with the tissue of the patient. While ultrasound probe 104 is in the first contact state, the average pixel classification must go below a second contact state threshold that is lower than the first contact state threshold for system 300 to determine that ultrasound probe 104 is in the second contact state that indicates that the ultrasound probe 104 is not in operative physical contact with the tissue of the patient.

System 300 may determine the contact state of ultrasound probe 104 in any other suitable manner. For example, system 300 may provide the classifications to a machine learning model and use an output of the machine learning model to determine the contact state of ultrasound probe 104. As another example, system 300 may evaluate any suitable function based on the classifications to determine the contact state of ultrasound probe 104.

In some examples, before determining the local descriptor values, system 300 may optionally determine a background intensity for ultrasound image 114 and generate a demeaned ultrasound image by subtracting the background intensity from the ultrasound image 114. System 300 may then determine the local descriptor values for the pixels in ultrasound image 114 by determining the local descriptor values for pixels included in the demeaned ultrasound image.

A particular processing heuristic that may be performed by system 300 in accordance with the principles described herein to determine a contact state of ultrasound probe 104 will now be described. It will be recognized that the processing heuristic is exemplary of a variety of different processing heuristics that may be performed by system 300 to determine a contact state of ultrasound probe 104.

As mentioned, ultrasound images can appear to be noisy due to speckle. However, the intensity distribution and spatial autocorrelation of speckle differs from noise. Since the image content and gain settings can vary throughout the image, the autocovariance function may be estimated locally in accordance with the following equation: $W_{j,k}(x, y)=E[(I(x, y)-\mu(x, y))(I(x+j, y+k)-\mu(x+j, y+k))]$.

In this equation, $W_{j,k}(x, y)$ is the spatial autocovariance at location x and y, $I(x, y)$ is the image intensity value, and $\mu(x, y)$ is the local mean intensity.

To distinguish between noise and speckle (which is representative of tissue), system 300 may determine the local mean intensity and one or more terms (also referred to as coefficients) of the autocovariance function.

For example, system 300 may first perform background subtraction on ultrasound image 114. To illustrate, system 300 may use a box filter, $H_1$ (e.g., a seven by seven pixel filter) to estimate the background intensity and then subtract the background intensity from the original ultrasound image 114 to produce a demeaned image, $\tilde{I}$, where $\tilde{I}(x, y)=I(x, y)-H_1*I(x, y)$.

System 300 may then determine one or more terms of the autocovariance function. For example, system 300 may determine an estimate, $\hat{W}_{j,k}$, within a local neighborhood around each pixel. For example, system 300 may use a second box filter, $H_2$, (e.g., a 13 by 13 pixel filter) in accordance with the following equations: $\hat{W}_{0,0}(x, y)=H_2*\tilde{I}(x, y)^2$ and $\hat{W}_{0,1}(x, y)=H_2*(\tilde{I}(x, y)\cdot\tilde{I}(x, y+1))$.

System 300 may then generate a binary tissue map, T(x, y), which shows which pixels are consistent with signal coming from ultrasound reflected or backscattered from tissue. For example, the binary tissue map may be generated in accordance with the following equation: $T(x, y)=\hat{W}_{0,0}(x, y)>V$ & $\hat{W}_{0,1}(x, y)/\hat{W}_{0,0}(x, y)>AC1$.

In this equation, V and AC1 are threshold parameters corresponding to the minimum variance and lag-1 autocorrelation in the vertical direction. In the examples herein, autocorrelation is the autocovariance function normalized by the variance (i.e., $\hat{W}_{j,k}(x, y)/\hat{W}_{0,0}(x, y)$).

System 300 may optionally apply morphological processing to remove isolated pixels from T(x, y) and produce a smoother map. The morphological processing may be performed in any suitable manner.

System 300 may use the ratio of pixels within region of interest 404 where tissue is detected to determine the contact state of ultrasound probe 104 in accordance with the following equation: $\Sigma_{ROI}T(x, y)/N_{ROI}$.

In some examples, to prevent bouncing between contact states, two thresholds may be used by system 300. For example, if $\Sigma_{ROI}T(x, y)/N_{ROI}$ is goes above a first contact state threshold, system 300 may determine that ultrasound probe 104 is in a first contact state that indicates that ultrasound probe 104 is in operative physical contact with the tissue of the patient. Once in this state, $\Sigma_{ROI}T(x, y)/_{ROI}$ must go below a second contact state threshold lower than the first contact state threshold before system 300 determines that ultrasound probe 104 is in a second contact state that indicates that ultrasound probe 104 is not in operative physical contact with the tissue of the patient.

In some alternative embodiments, system 300 may obtain local estimates of the autocovariance function by using frequency domain approaches based on the short-time Fourier transform (STFT) or wavelet transforms. The STFT coefficients, or those of another wavelet transform, could be used directly to generate the tissue map described herein. In some examples, the coefficients of the auto-covariance function described herein may be replaced with those of an STFT or wavelet transform.

In some examples, any of the thresholds described herein (e.g., the local descriptor thresholds and the contact state thresholds described herein) may be set by system 300 in response to user input. In this manner, a user may manually tune the thresholds to appropriate levels. Additionally or alternatively, any of the thresholds described herein may be set based on an output of a machine learning model. The thresholds described herein may additionally or alternatively be determined in any other manner.

System 300 may perform various operations based on the contact state of ultrasound probe 104. For example, based on the contact state of ultrasound probe 104, system 300 may control a display of ultrasound image 114 within a viewable image displayed by display device 106.

Figure 5A:
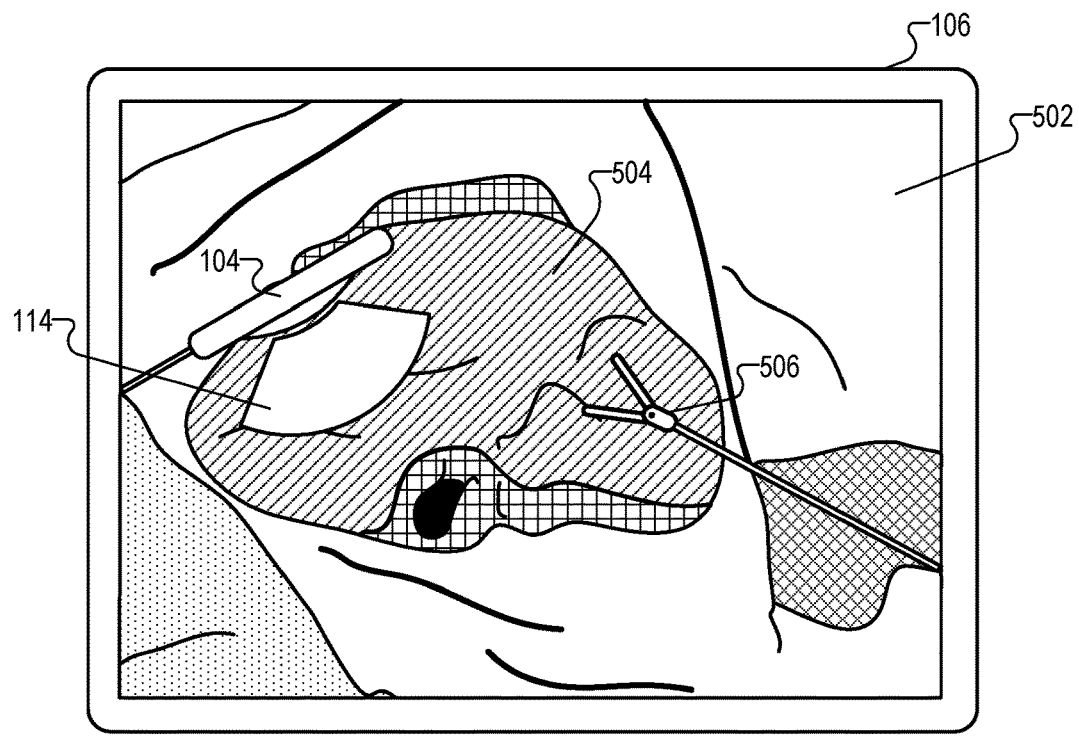
FIGS. 5A-5B show an exemplary viewable image displayed by a display device according to principles described herein.
Figure 5B:
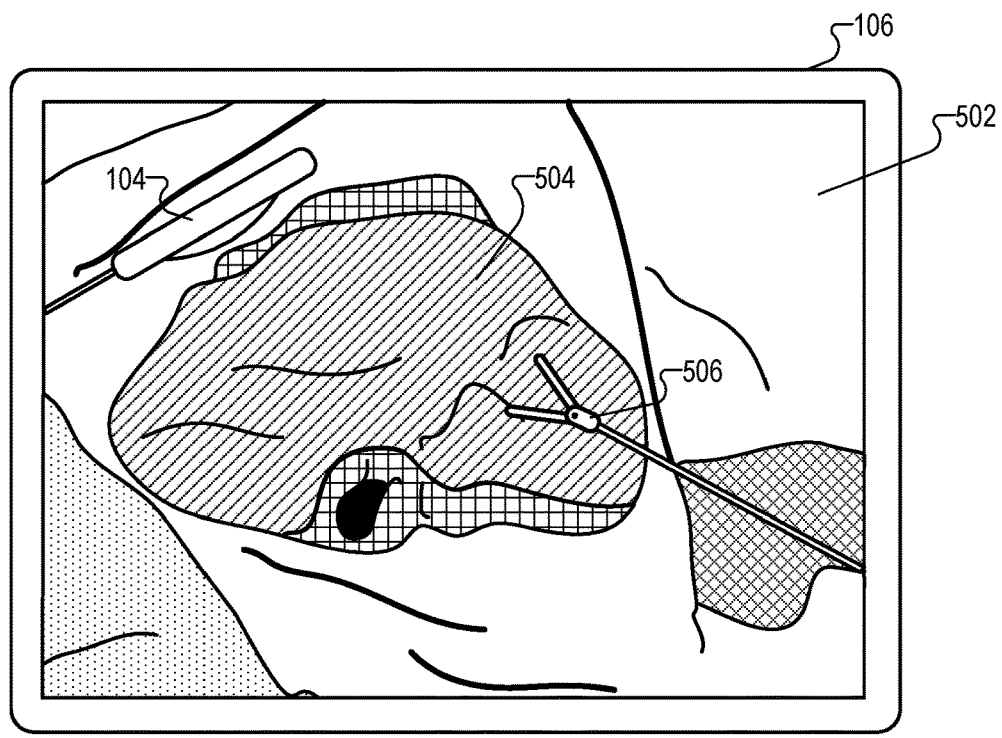

To illustrate, FIGS. 5A-5B show an exemplary viewable image 502 displayed by display device 106. Viewable image 502 includes an endoscopic image of a surgical area within a patient as captured by an endoscope. As shown in both FIGS. 5A-5B, the endoscopic image depicts tissue 504 (e.g., an organ within the patient), a surgical tool 506 configured to manipulate tissue 504 in response to user input, and ultrasound probe 104, While viewable image 502 is depicted as a two-dimensional image in FIGS. 5A-5B, it will be recognized that viewable image 502 may alternatively be a three-dimensional image in other examples.

In some examples, viewable image 502 may further include a pre-operative model of patient anatomy within the surgical area depicted in viewable image 502. This is described more fully in U.S. Provisional Patent Application No. 62/855,755, the contents of which are incorporated herein by reference in their entirety. The pre-operative model may be registered with the endoscopic image such that the model is located at a position within viewable image 502 that corresponds to an actual position of the patient anatomy. For example, the pre-operative model may include a three-dimensional model of structures interior to tissue 504 generated based on pre-operative imaging (e.g., MRI and/or CT scan imaging).

In FIG. 5A, ultrasound probe 104 is in operative physical contact with tissue 504. Accordingly, system 300 may determine that the contact state of ultrasound probe 104 indicates that ultrasound probe 104 is in operative physical contact with tissue 504. Based on this determination and as shown in FIG. 5A, system 300 may display ultrasound image 114 within viewable image 502. As illustrated, ultrasound image 114 may be located within viewable image 502 at a position that appears to be directly beneath the bottom surface of ultrasound probe 104. By positioning ultrasound image 114 in this manner, system 300 may allow a user to more readily ascertain relative positions of structures interior to tissue 504 and included within ultrasound image 114 with other content shown in viewable image 502. Alternatively, ultrasound image 114 may be located at any other position within viewable image 502 as may serve a particular implementation.

FIG. 5B shows that ultrasound probe 104 has been repositioned to a location that is not in physical contact with tissue 504. Such repositioning may occur in response to user manipulation of ultrasound probe 104 and/or in any other manner. In response to the repositioning, system 300 may determine that the contact state of ultrasound probe now indicates that ultrasound probe is not in operative physical contact with tissue 504. In response and as shown in FIG.

5B, system 300 may abstain from displaying (e.g., by hiding or otherwise not displaying) ultrasound image 114 in viewable image 502.

By intelligently controlling the display of ultrasound image 114 in this manner, system 300 may ensure that ultrasound image 114 is only displayed when it includes useful information for the user. Otherwise, ultrasound image 114 is hidden so as not to obscure other content in viewable image 502.

In some examples, system 300 may display only a portion of ultrasound image 114 in response to determining that the contact state of ultrasound probe 104 indicates that ultrasound probe 104 is in operative physical contact with tissue 504. For example, if a particular region (e.g., a pie-shaped slice) of ultrasound image 114 includes useful information, but the rest of ultrasound image 114 does not, this may be indicative of only a portion of ultrasound probe 104 being in operative physical contact with tissue 504. In response, system 300 may generate and display a cropped ultrasound image that includes only a portion of ultrasound image 114. The cropped ultrasound image may include the region that includes the useful information and may be determined based on the classification of the pixels as either showing tissue or showing non-tissue.

Figure 6A:
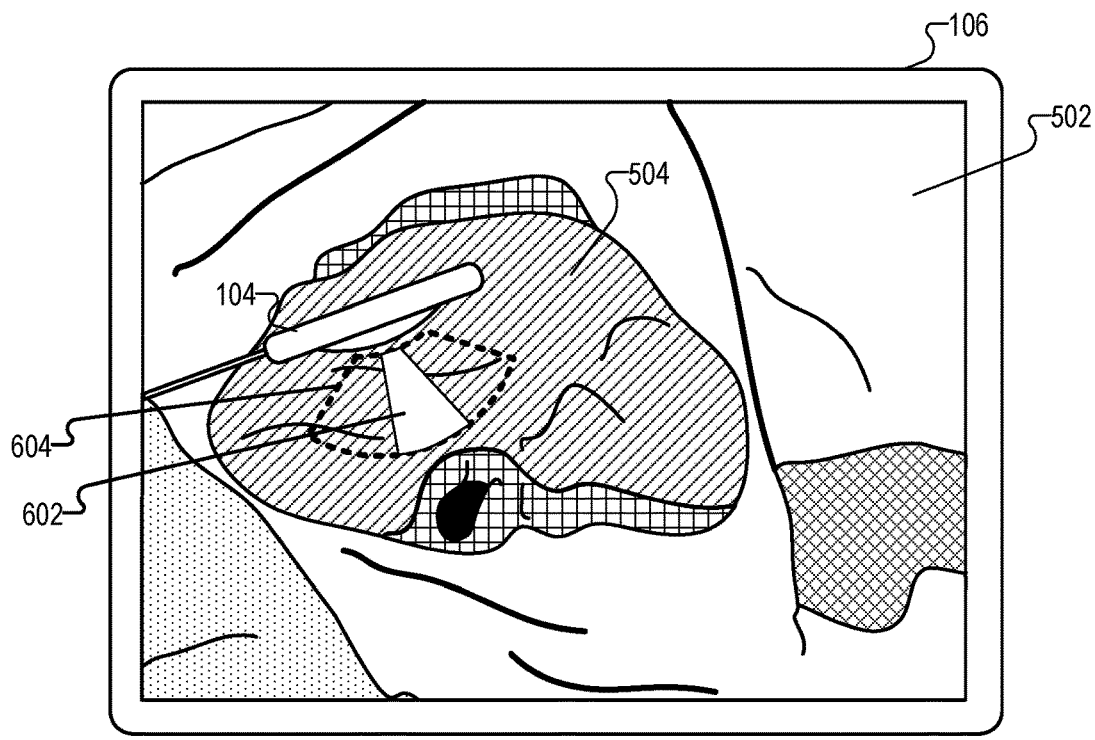
FIGS. 6A-6B show an exemplary viewable image displayed by a display device according to principles described herein.

To illustrate, FIG. 6A shows viewable image 502 displayed by display device 106. As shown, instead of displaying the full ultrasound image 114 within viewable image 502, system 300 displays a cropped ultrasound image 602 within viewable image 502. For the sake of comparison, a dashed outline 604 representative of what full ultrasound image 114 would look like were it displayed is shown in FIG. 6A. Dashed outline 604 may or may not be actually displayed in viewable image 502 as may serve a particular implementation.

Figure 6B:
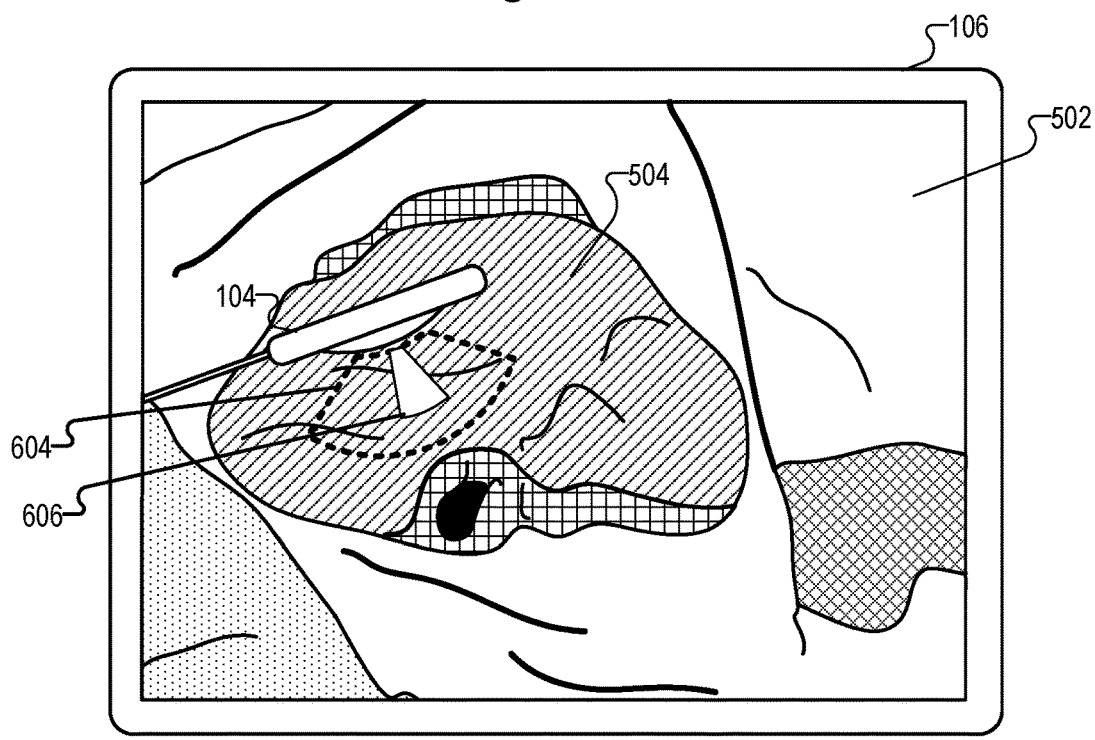

FIG. 6B illustrates another example of displaying only a portion of ultrasound image 114 in viewable image 502. In this example, system 300 displays cropped ultrasound image 606 instead of full ultrasound image 114, which is again represented by dashed lines 604 that may or may not be actually displayed in viewable image 502. As shown, cropped ultrasound image 606 does not include a distal region of full ultrasound image 114. This type of cropped ultrasound image 606 may be beneficial to display in scenarios in which deeper regions of tissue result in signal dropout, thus causing the distal region of full ultrasound image 114 to include more noise than useful content.

System 300 may additionally or alternatively set (e.g., adjust), based on the contact state of ultrasound probe 104, a parameter of ultrasound imaging machine 102. For example, system 300 may set a frequency and/or a gain of the sound emitted or received by ultrasound probe 104 based on the contact state of ultrasound probe 104. System 300 may additionally or alternatively set a fan depth for ultrasound image 114 based on the contact state of ultrasound probe 104. By setting one or more parameters based on the contact state of ultrasound probe 104, system 300 may be configured to automatically acquire a better quality ultrasound image 114.

For example, the contact state of ultrasound probe 104 may indicate that ultrasound probe 102 is barely in operative physical contact with tissue 504 (e.g., if the ratio described above is barely above the contact state threshold). In this scenario, system 300 may increase the gain of the sound received by ultrasound probe 104 to improve the image quality of ultrasound image 114.

System 300 may additionally or alternatively generate, based on the contact state of ultrasound probe 104, a control signal configured to be used by a computer-assisted surgical system to control a positioning of ultrasound probe 104 (e.g., to achieve and/or maintain tissue contact). For example, a shaft of ultrasound probe 104 may be coupled to a manipulator arm of a computer-assisted surgical system. In this example, the computer-assisted surgical system may be configured to adjust a positioning of ultrasound probe 104 based on the control signal by repositioning the manipulator arm. As another example, a different surgical tool (e.g., graspers) controllable by computer-assisted surgical system may be configured to hold and reposition ultrasound probe 104. In either example, the control signal may indicate that ultrasound probe 102 is not in operative physical contact with tissue 504. In response, the computer-assisted surgical system may reposition ultrasound probe 104 until the control signal indicates that ultrasound probe 102 is in operative physical contact with tissue 504.

Figure 7:
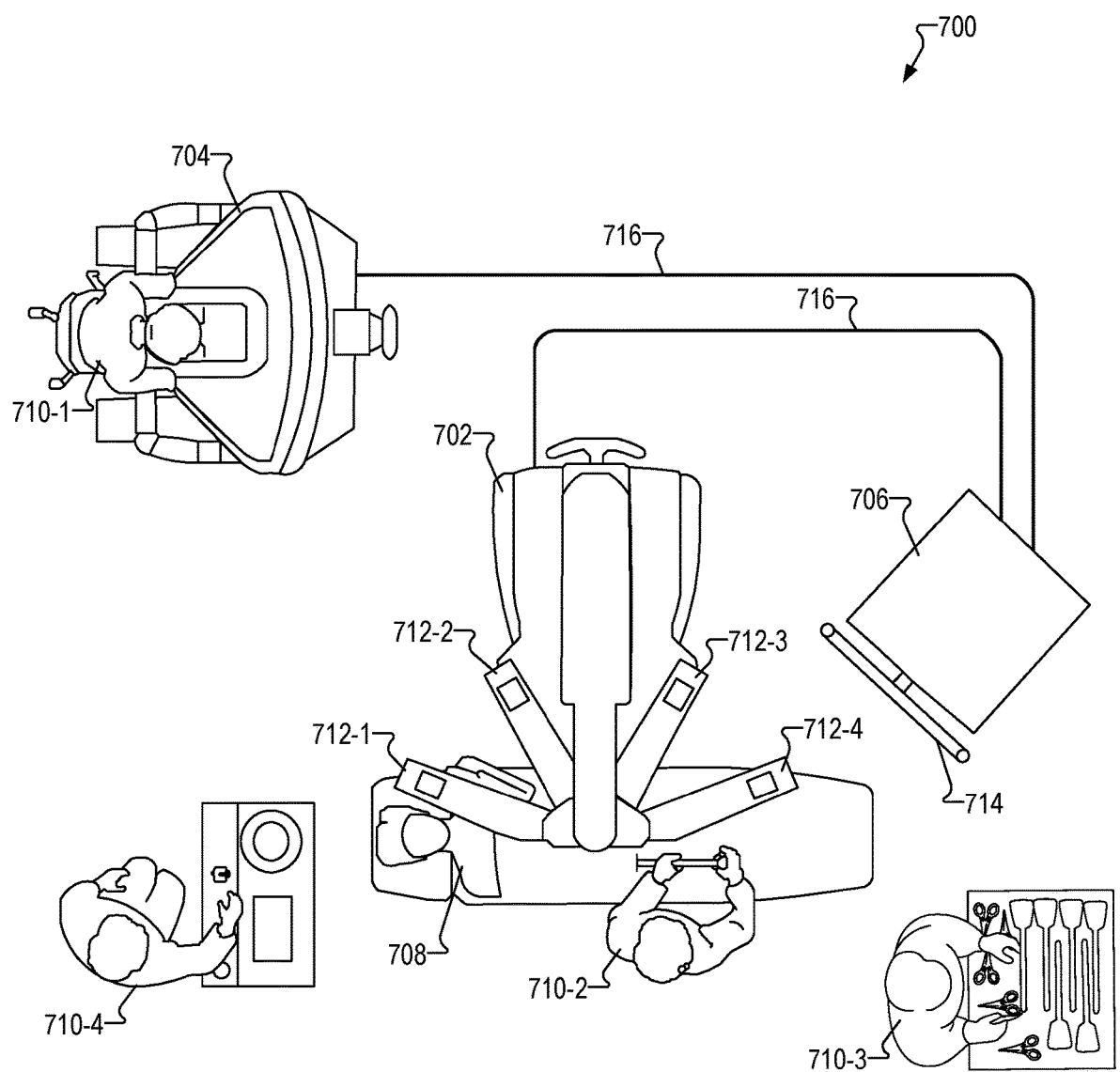
FIG. 7 illustrates an exemplary computer-assisted surgical system according to principles described herein.

FIG. 7 illustrates an exemplary computer-assisted surgical system 700 ("surgical system 700"). As described herein, ultrasound machine 102 and system 300 may be implemented by surgical system 700, connected to surgical system 700, and/or otherwise used in conjunction with surgical system 700.

As shown, surgical system 700 may include a manipulating system 702, a user control system 704, and an auxiliary system 706 communicatively coupled one to another. Surgical system 700 may be utilized by a surgical team to perform a computer-assisted surgical procedure on a patient 708. As shown, the surgical team may include a surgeon 710-1, an assistant 710-2, a nurse 710-3, and an anesthesiologist 710-4, all of whom may be collectively referred to as "surgical team members 710," Additional or alternative surgical team members may be present during a surgical session as may serve a particular implementation.

While FIG. 7 illustrates an ongoing minimally invasive surgical procedure, it will be understood that surgical system 700 may similarly be used to perform open surgical procedures or other types of surgical procedures that may similarly benefit from the accuracy and convenience of surgical system 700. Additionally, it will be understood that the surgical session throughout which surgical system 700 may be employed may not only include an operative phase of a surgical procedure, as is illustrated in FIG. 7, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 7, manipulating system 702 may include a plurality of manipulator arms 712 (e.g., manipulator arms 712-1 through 712-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 708 (e.g., by being at least partially inserted into patient 708 and manipulated to perform a computer-assisted surgical procedure on patient 708). While manipulating system 702 is depicted and described herein as including four manipulator arms 712, it will be recognized that manipulating system 702 may include only a single manipulator arm 712 or any other number of manipulator arms as may serve a particular implementation.

Manipulator arms 712 and/or surgical instruments attached to manipulator arms 712 may include one or more displacement transducers, orientational sensors, and/or positional sensors used to generate raw (i.e., uncorrected) kinematics information. One or more components of surgical system 700 may be configured to use the kinematics information to track (e.g., determine positions of) and/or control the surgical instruments.

User control system 704 may be configured to facilitate control by surgeon 710-1 of manipulator arms 712 and surgical instruments attached to manipulator arms 712. For example, surgeon 710-1 may interact with user control system 704 to remotely move or manipulate manipulator arms 712 and the surgical instruments. To this end, user control system 704 may provide surgeon 710-1 with imagery (e.g., high-definition 3D imagery) of a surgical area associated with patient 708 as captured by an imaging system (e.g., any of the medical imaging systems described herein). In certain examples, user control system 704 may include a stereo viewer having two displays where stereoscopic images of a surgical area associated with patient 708 and generated by a stereoscopic imaging system may be viewed by surgeon 710-1. Surgeon 710-1 may utilize the imagery to perform one or more procedures with one or more surgical instruments attached to manipulator arms 712.

To facilitate control of surgical instruments, user control system 704 may include a set of master controls. These master controls may be manipulated by surgeon 710-1 to control movement of surgical instruments (e.g., by utilizing robotic and/or teleoperation technology). The master controls may be configured to detect a wide variety of hand, wrist, and finger movements by surgeon 710-1. In this manner, surgeon 710-1 may intuitively perform a procedure using one or more surgical instruments.

Auxiliary system 706 may include one or more computing devices configured to perform primary processing operations of surgical system 700. In such configurations, the one or more computing devices included in auxiliary system 706 may control and/or coordinate operations performed by various other components (e.g., manipulating system 702 and user control system 704) of surgical system 700. For example, a computing device included in user control system 704 may transmit instructions to manipulating system 702 by way of the one or more computing devices included in auxiliary system 706. As another example, auxiliary system 706 may receive, from manipulating system 702, and process image data representative of imagery captured by an imaging device attached to one of manipulator arms 712.

In some examples, auxiliary system 706 may be configured to present visual content to surgical team members 710 who may not have access to the images provided to surgeon 710-1 at user control system 704. To this end, auxiliary system 706 may include a display monitor 714 configured to display one or more user interfaces, such as images (e.g., 2D images) of the surgical area, information associated with patient 708 and/or the surgical procedure, and/or any other visual content as may serve a particular implementation. For example, display monitor 714 may display images of the surgical area together with additional content (e.g., graphical content, contextual information, etc.) concurrently displayed with the images. In some embodiments, display monitor 714 is implemented by a touchscreen display with which surgical team members 710 may interact (e.g., by way of touch gestures) to provide user input to surgical system 700.

Manipulating system 702, user control system 704, and auxiliary system 706 may be communicatively coupled one to another in any suitable manner. For example, as shown in FIG. 7, manipulating system 702, user control system 704, and auxiliary system 706 may be communicatively coupled by way of control lines 716, which may represent any wired or wireless communication link as may serve a particular implementation. To this end, manipulating system 702, user control system 704, and auxiliary system 706 may each include one or more wired or wireless communication interfaces, such as one or more local area network interfaces, Wi-Fi network interfaces, cellular interfaces, etc.

Figure 8:
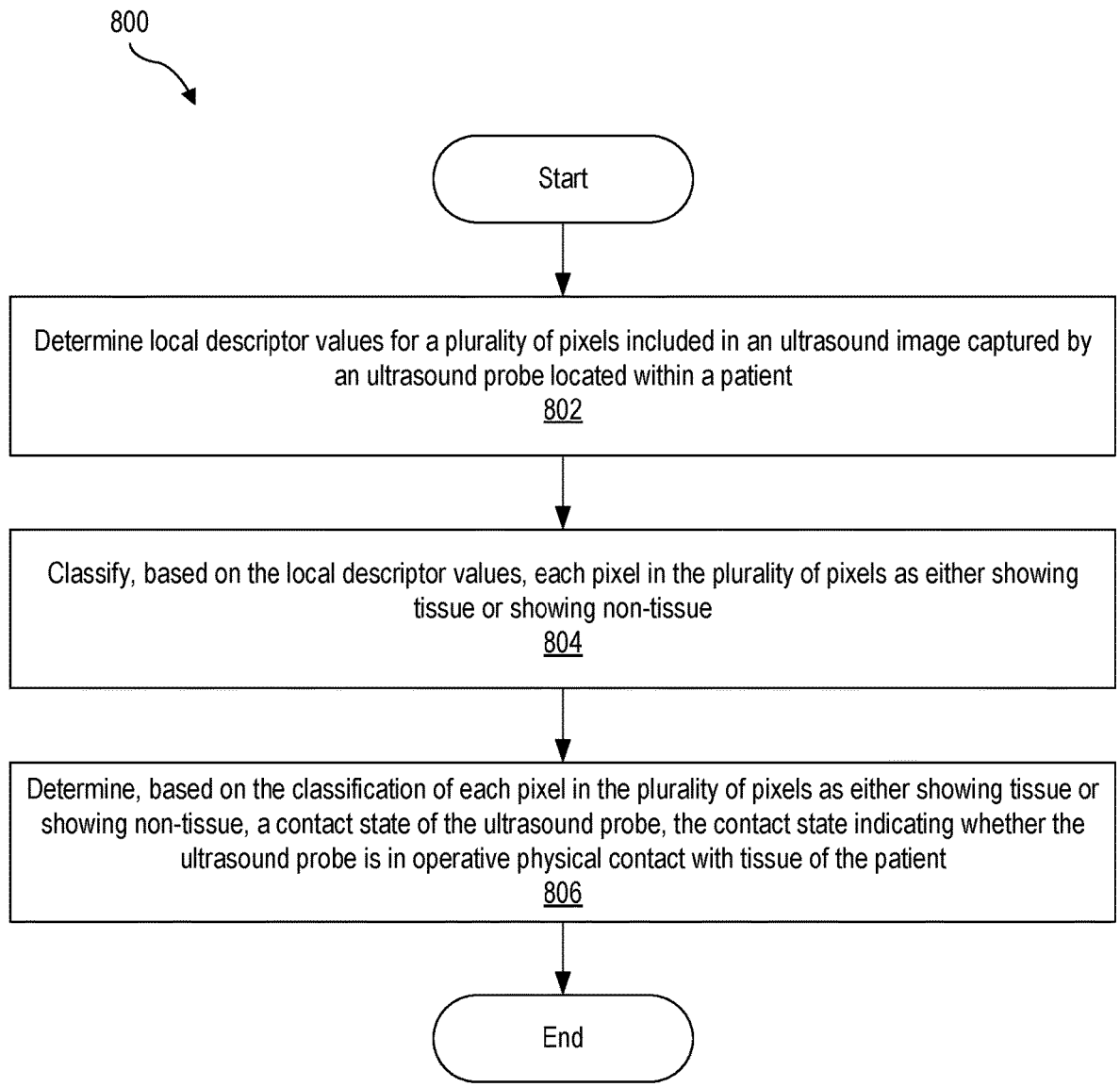
FIGS. 8-12 show exemplary methods according to principles described herein.

FIG. 8 shows an exemplary method 800. While FIG. 8 illustrates exemplary operations according to one embodiment, other embodiments may omit, add to, reorder, combine, and/or modify any of the steps shown in FIG. 8 One or more of the operations shown in in FIG. 8 may be performed by system 300, any components included therein, and/or any implementation thereof.

In operation 802, a contact detection system determines local descriptor values for a plurality of pixels included in an ultrasound image captured by an ultrasound probe located within a patient. Operation 802 may be performed in any of the ways described herein.

In operation 804, the contact detection system classifies, based on the local descriptor values, each pixel in the plurality of pixels as either showing tissue or showing non-tissue. Operation 804 may be performed in any of the ways described herein.

In operation 806, the contact detection system determines, based on the classification of each pixel in the plurality of pixels as either showing tissue or showing non-tissue, a contact state of the ultrasound probe, the contact state indicating whether the ultrasound probe is in operative physical contact with tissue of the patient. Operation 806 may be performed in any of the ways described herein.

Figure 9:
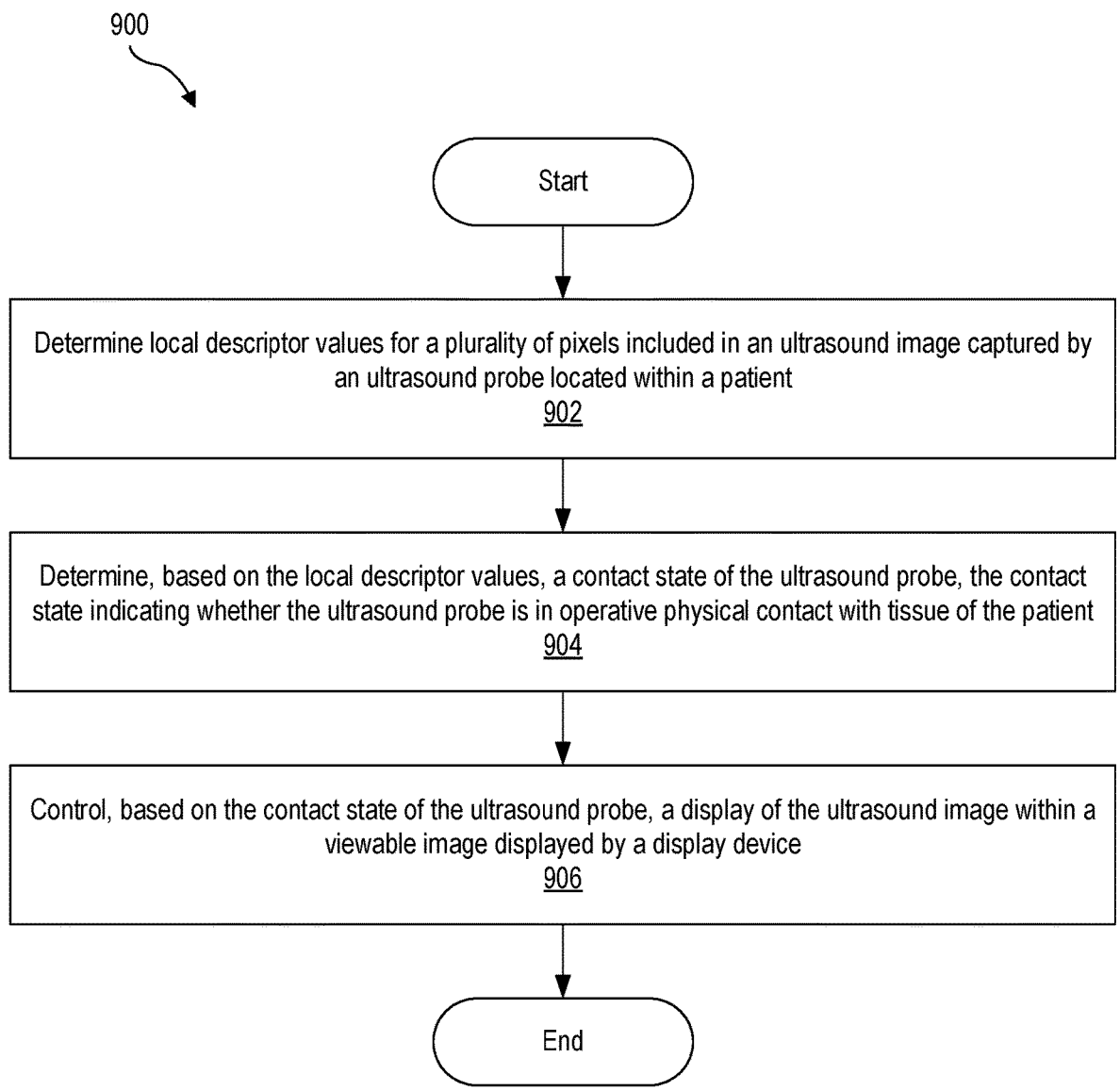

FIG. 9 shows another exemplary method 900. While FIG. 9 illustrates exemplary operations according to one embodiment, other embodiments may omit, add to, reorder, combine, and/or modify any of the steps shown in FIG. 9 One or more of the operations shown in in FIG. 9 may be performed by system 300, any components included therein, and/or any implementation thereof.

In operation 902, a contact detection system determines local descriptor values for a plurality of pixels included in an ultrasound image captured by an ultrasound probe located within a patient. Operation 902 may be performed in any of the ways described herein.

In operation 904, the contact detection system determines, based on the local descriptor values, a contact state of the ultrasound probe, the contact state indicating whether the ultrasound probe is in operative physical contact with tissue of the patient. Operation 904 may be performed in any of the ways described herein.

In operation 906, the contact detection system controls, based on the contact state of the ultrasound probe, a display of the ultrasound image within a viewable image displayed by a display device. Operation 906 may be performed in any of the ways described herein.

Figure 10:
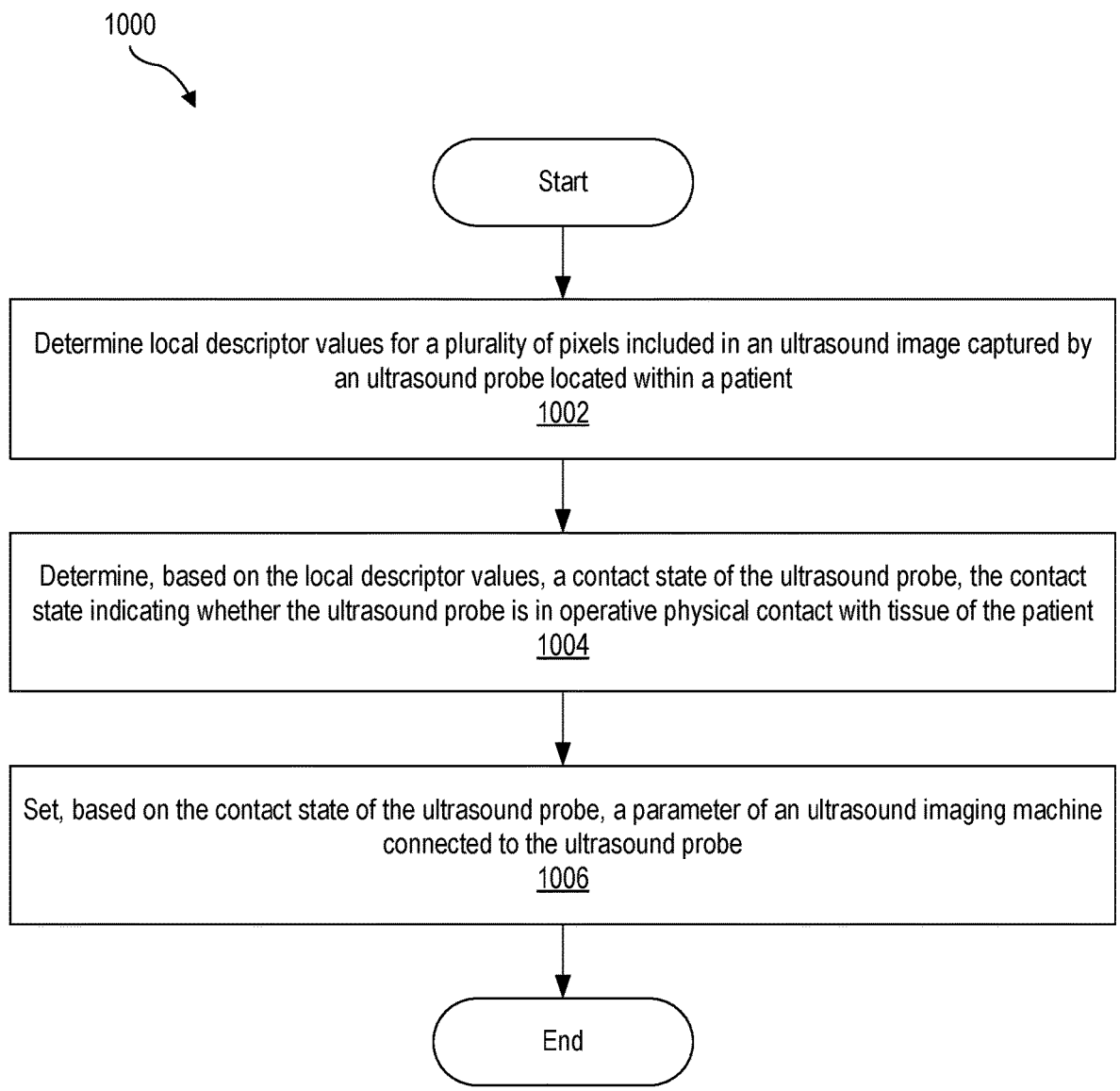

FIG. 10 shows another exemplary method 1000. While FIG. 10 illustrates exemplary operations according to one embodiment, other embodiments may omit, add to, reorder, combine, and/or modify any of the steps shown in FIG. 10 One or more of the operations shown in in FIG. 10 may be performed by system 300, any components included therein, and/or any implementation thereof.

In operation 1002, a contact detection system determines local descriptor values for a plurality of pixels included in an ultrasound image captured by an ultrasound probe located within a patient. Operation 1002 may be performed in any of the ways described herein.

In operation 1004, the contact detection system determines, based on the local descriptor values, a contact state of the ultrasound probe, the contact state indicating whether the ultrasound probe is in operative physical contact with tissue of the patient. Operation 1004 may be performed in any of the ways described herein.

In operation 1006, the contact detection system sets, based on the contact state of the ultrasound probe, a parameter of an ultrasound imaging machine connected to the ultrasound probe. Operation 1006 may be performed in any of the ways described herein.

Figure 11:
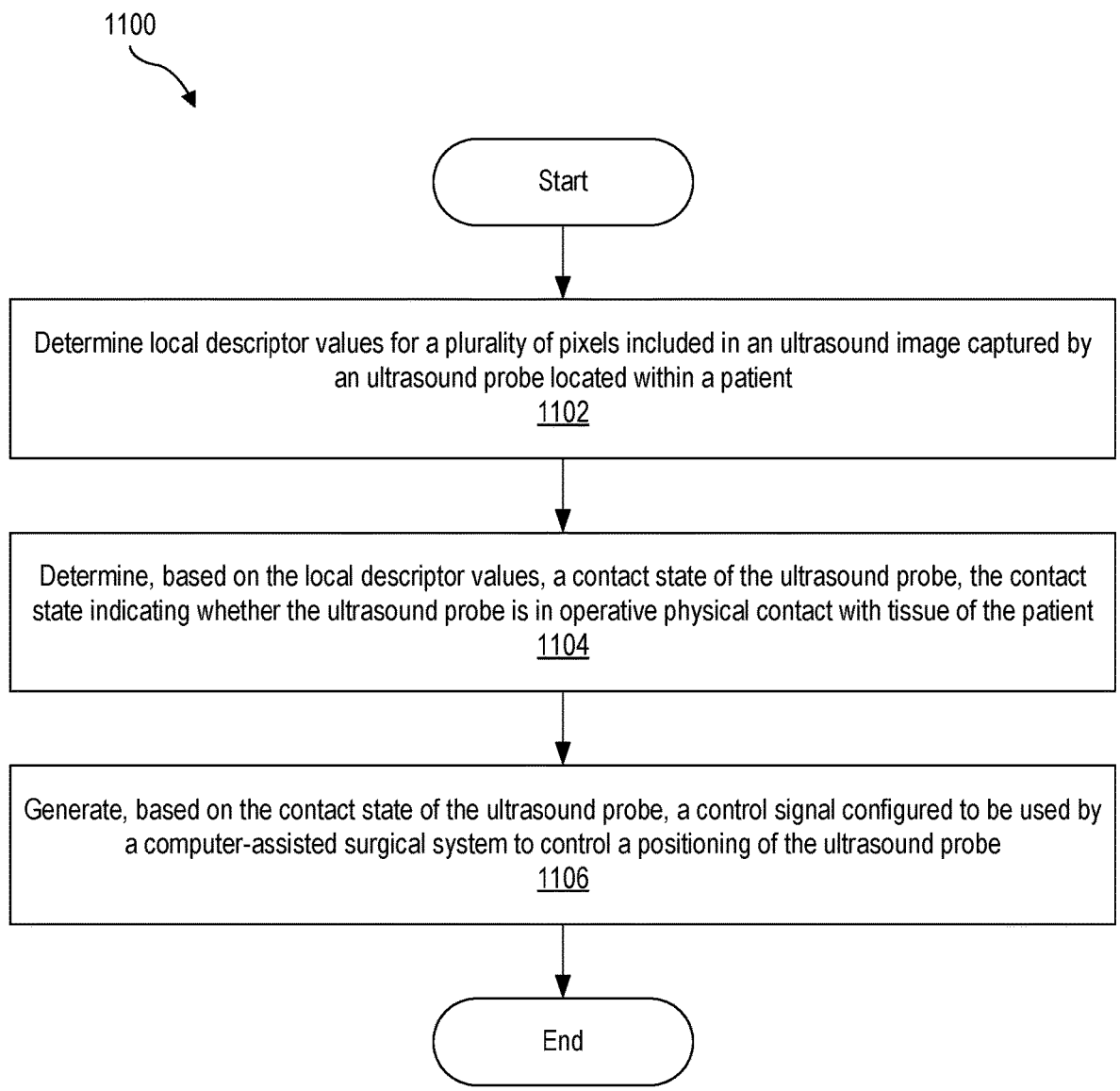

FIG. 11 shows another exemplary method 1100. While FIG. 11 illustrates exemplary operations according to one embodiment, other embodiments may omit, add to, reorder, combine, and/or modify any of the steps shown in FIG. 11 One or more of the operations shown in in FIG. 11 may be performed by system 300, any components included therein, and/or any implementation thereof.

In operation 1102, a contact detection system determines local descriptor values for a plurality of pixels included in an ultrasound image captured by an ultrasound probe located within a patient. Operation 1102 may be performed in any of the ways described herein.

In operation 1104, the contact detection system determines, based on the local descriptor values, a contact state of the ultrasound probe, the contact state indicating whether the ultrasound probe is in operative physical contact with tissue of the patient. Operation 1104 may be performed in any of the ways described herein.

In operation 1106, the contact detection system generates, based on the contact state of the ultrasound probe, a control signal configured to be used by a computer-assisted surgical system to control a positioning of the ultrasound probe. Operation 1106 may be performed in any of the ways described herein.

Figure 12:
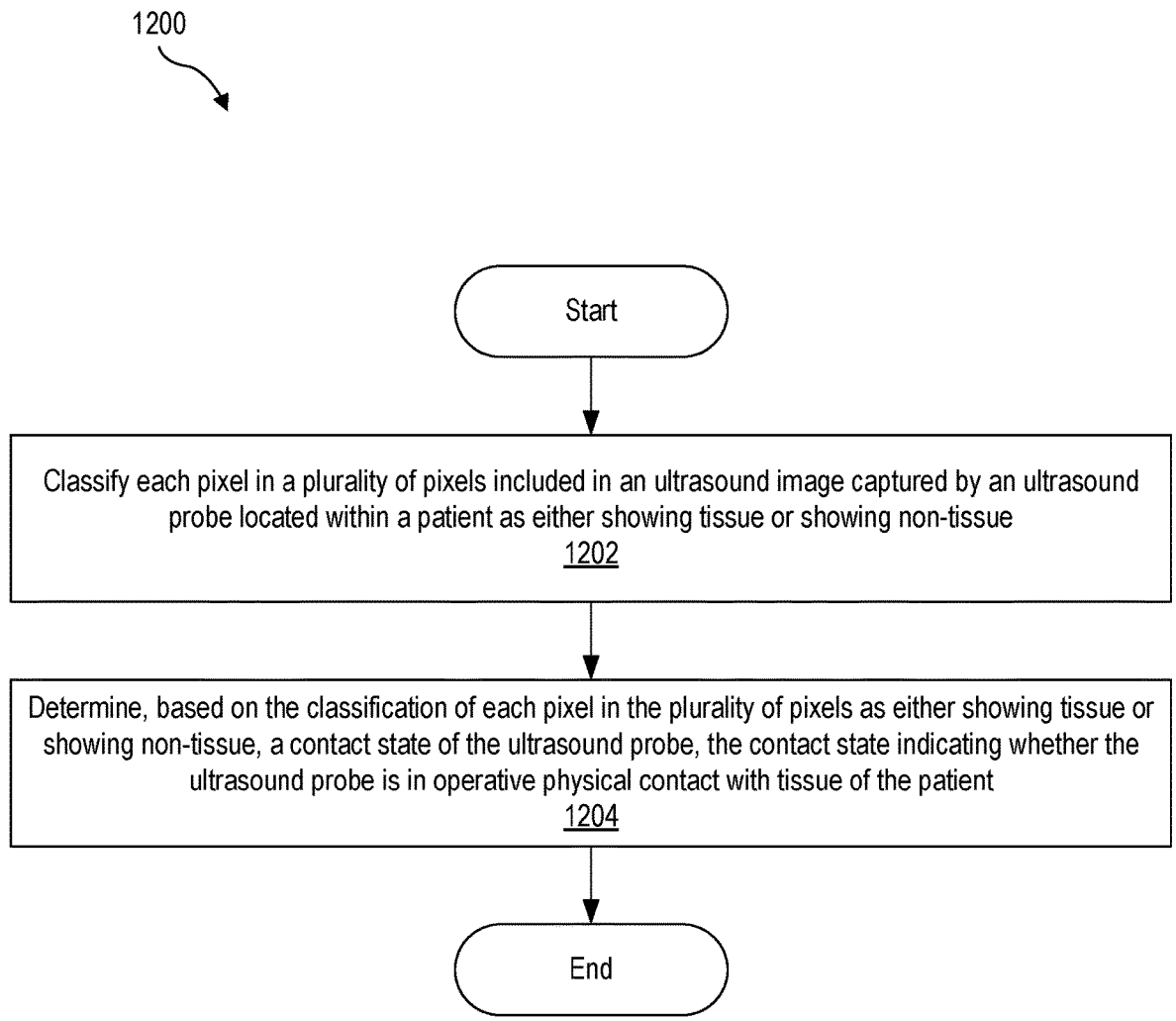

FIG. 12 shows another exemplary method 1200. While FIG. 12 illustrates exemplary operations according to one embodiment, other embodiments may omit, add to, reorder, combine, and/or modify any of the steps shown in FIG. 12 One or more of the operations shown in in FIG. 12 may be performed by system 300, any components included therein, and/or any implementation thereof.

In operation 1202, a contact detection system classifies each pixel in a plurality of pixels included in an ultrasound image captured by an ultrasound probe located within a patient as either showing tissue or showing non-tissue. Operation 1202 may be performed in any of the ways described herein.

In operation 1204, the contact detection system determines, based on the classification of each pixel in the plurality of pixels as either showing tissue or showing non-tissue, a contact state of the ultrasound probe, the contact state indicating whether the ultrasound probe is in operative physical contact with tissue of the patient. Operation 1204 may be performed in any of the ways described herein.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 13:
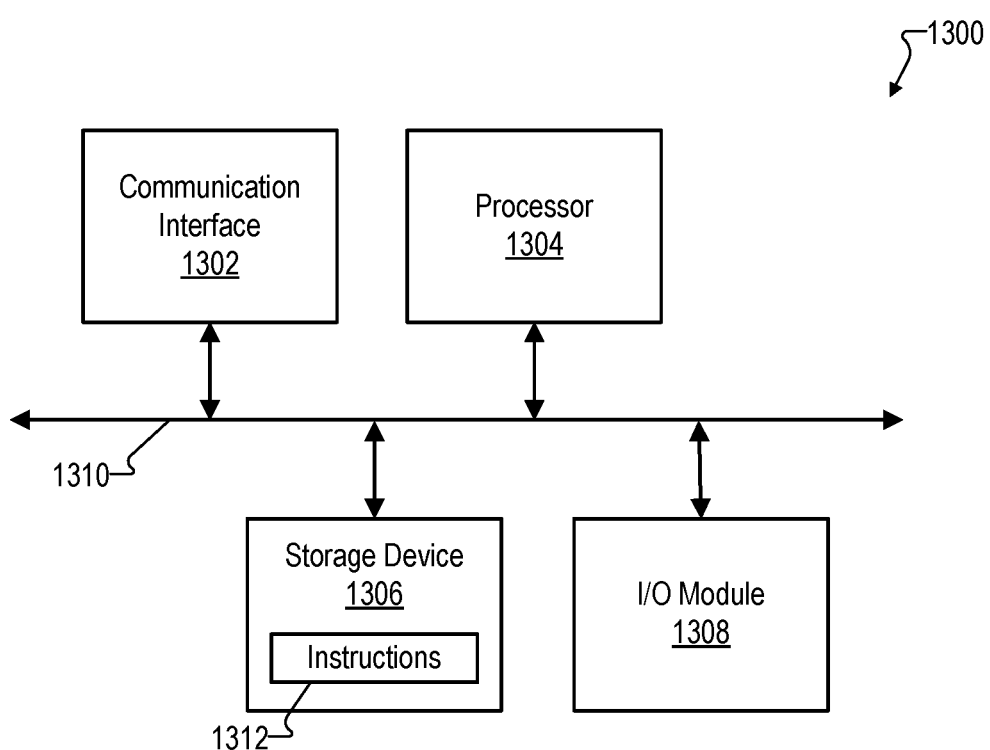
FIG. 13 illustrates an exemplary computing device according to principles described herein.

FIG. 13 illustrates an exemplary computing device 1300 that may be specifically configured to perform one or more of the processes described herein. Any of the systems, units, computing devices, and/or other components described herein may be implemented by computing device 1300.

As shown in FIG. 13, computing device 1300 may include a communication interface 1302, a processor 1304, a storage device 1306, and an input/output ("I/O") module 1308 communicatively connected one to another via a communication infrastructure 1310. While an exemplary computing device 1300 is shown in FIG. 13, the components illustrated in FIG. 13 are not intended to be limiting. Additional or alternative components may be used in other embodiments. Components of computing device 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data and/or interpreting, executing, and/or directing execution of one or more of the instructions, processes, and/or operations described herein. Processor 1304 may perform operations by executing computer-executable instructions 1312 (e.g., an application, software, code, and/or other executable data instance) stored in storage device 1306.

Storage device 1306 may include one or more data storage media, devices, or configurations and may employ any type, form, and combination of data storage media and/or device. For example, storage device 1306 may include, but is not limited to, any combination of the non-volatile media and/or volatile media described herein. Electronic data, including data described herein, may be temporarily and/or permanently stored in storage device 1306. For example, data representative of computer-executable instructions 1312 configured to direct processor 1304 to perform any of the operations described herein may be stored within storage device 1306. In some examples, data may be arranged in one or more databases residing within storage device 1306.

I/O module 1308 may include one or more modules configured to receive user input and provide user output. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A computer-assisted surgical system comprising:
   a manipulator arm configured to be coupled to an ultrasound probe and to position the ultrasound probe within a patient; and
   one or more processors configured to:
     generate an ultrasound image based on sound waves detected by the ultrasound probe while located within the patient;
     determine a plurality of local descriptor values each corresponding to a different pixel included in a plurality of pixels included in the ultrasound image, the plurality of pixels including at least a first pixel corresponding to a first local descriptor value included in the plurality of local descriptor values and a second pixel corresponding to a second local descriptor value included in the plurality of local descriptor values;
     classify each pixel in the plurality of pixels individually as either showing tissue or showing non-tissue, the classifying comprising classifying the first pixel as showing tissue or showing non-tissue based only on the first local descriptor value and classifying the second pixel as showing tissue or showing non-tissue based only on the second local descriptor value;
     determine an average pixel classification representative of a number of pixels included in the plurality of pixels and individually classified as showing tissue compared to a number of pixels included in the plurality of pixels and individually classified as showing non-tissue;
     determine, if the average pixel classification is above a first contact state threshold, that the ultrasound probe is in a first contact state that indicates that the ultrasound probe is in operative physical contact with the tissue of the patient; and
     determine, if the average pixel classification is below a second contact state threshold lower than the first contact state threshold, that the ultrasound probe is in a second contact state that indicates that the ultrasound probe is not in operative physical contact with the tissue of the patient.

2. The computer-assisted surgical system of claim 1, where in the local descriptor values characterize at least one of an intensity distribution and a spatial autocorrelation for each pixel in the plurality of pixels.

3. The computer-assisted surgical system of claim 1, wherein the classifying comprises:
   providing the local descriptor values as inputs into a machine learning model, and
   classifying, based on an output of the machine learning model, each pixel in the plurality of pixels as either showing tissue or showing non-tissue.

4. The computer-assisted surgical system of claim 1, wherein the local descriptor values comprise one or more of local variance values for the plurality of pixels or autocorrelation values for the plurality of pixels.

5. The computer-assisted surgical system of claim 4, wherein:
   the determining of the local descriptor values for the plurality of pixels comprises determining both a local variance value and an autocorrelation value for each pixel included in the plurality of pixels;
   the classifying comprises
     classifying pixels in the ultrasound image that have local variance values above a variance threshold and autocorrelation values above an autocorrelation threshold as showing tissue, and
     classifying pixels in the ultrasound image that have local variance values below the variance threshold or autocorrelation values below the autocorrelation threshold as showing non-tissue.

6. The computer-assisted surgical system of claim 1, wherein:
   the one or more processors are further configured to
     determine a background intensity for the ultrasound image, and
     generate a demeaned ultrasound image by subtracting the background intensity from the ultrasound image; and
   the determining of the local descriptor values for the plurality of pixels comprises determining the local descriptor values for pixels included in the demeaned ultrasound image.

7. The computer-assisted surgical system of claim 1, wherein the one or more processors are further configured control, based on the contact state of the ultrasound probe, a display of the ultrasound image within a viewable image displayed by a display device.

8. The computer-assisted surgical system of claim 7, wherein the viewable image includes an endoscopic image of a surgical area within the patient as captured by an endoscope.

9. The computer-assisted surgical system of claim 8, wherein the viewable image further includes a pre-operative model of patient anatomy within the surgical area of the patient, the pre-operative model registered with the endoscopic image.

10. The computer-assisted surgical system of claim 7, wherein the controlling of the display of the ultrasound image within the viewable image comprises:
    displaying the ultrasound image within the viewable image if the contact state indicates that the ultrasound probe is in operative physical contact with the tissue of the patient; and
    abstaining from displaying the ultrasound image within the viewable image if the contact state indicates that the ultrasound probe is not in operative physical contact with the tissue of the patient.

11. The computer-assisted surgical system of claim 7, wherein the controlling of the display of the ultrasound image within the viewable image comprises:
- determining that the contact state indicates that the ultrasound probe is in operative physical contact with the tissue of the patient;
- generating, in response to the determining that the contact state indicates that the ultrasound probe is in operative physical contact with the tissue of the patient and based on the classification of the pixels as either showing tissue or showing non-tissue, a cropped ultrasound image, the cropped ultrasound image including only a portion of the ultrasound image; and
- displaying the cropped ultrasound image within the viewable image.

12. The computer-assisted surgical system of claim 1, wherein the one or more processors are further configured to set, based on the contact state of the ultrasound probe, a parameter of an ultrasound imaging machine connected to the ultrasound probe.

13. The computer-assisted surgical system of claim 12, wherein the parameter comprises at least one of a frequency of sound emitted by the ultrasound probe, a gain of the sound received by the ultrasound probe, and a fan depth for the ultrasound image.

14. The computer-assisted surgical system of claim 1, wherein the one or more processors are further configured to generate, based on the contact state of the ultrasound probe, a control signal configured to be used by a computer-assisted surgical system to control a positioning of the ultrasound probe.

15. The computer-assisted surgical system of claim 1, wherein the plurality of pixels are included in a region of interest within the ultrasound image, the region of interest not including a set of pixels within the ultrasound image.

16. A method comprising:
- controlling, by one or more processors included in a computer-assisted surgical system, a manipulator arm coupled to an ultrasound probe to position the ultrasound probe within a patient;
- generating, by the one or more processors included in the computer-assisted surgical system, an ultrasound image based on sound waves detected by the ultrasound probe while located within the patient;
- determining, by the one or more processors included in the computer-assisted surgical system, a plurality of local descriptor values each corresponding to a different pixel included in a plurality of pixels included in the ultrasound image, the plurality of pixels including at least a first pixel corresponding to a first local descriptor value included in the plurality of local descriptor values and a second pixel corresponding to a second local descriptor value included in the plurality of local descriptor values;
- classifying, by the one or more processors included in the computer-assisted surgical system, each pixel in the plurality of pixels individually as either showing tissue or showing non-tissue, the classifying comprising classifying the first pixel as showing tissue or showing non-tissue based only on the first local descriptor value and classifying the second pixel as showing tissue or showing non-tissue based only on the second local descriptor value;
- determining, by the one or more processors included in the computer-assisted surgical system, an average pixel classification representative of a number of pixels included in the plurality of pixels and individually classified as showing tissue compared to a number of pixels included in the plurality of pixels and individually classified as showing non-tissue;
- determining, by the one or more processors included in the computer-assisted surgical system if the average pixel classification is above a first contact state threshold, that the ultrasound probe is in a first contact state that indicates that the ultrasound probe is in operative physical contact with the tissue of the patient; and
- determining, by the one or more processors included in the computer-assisted surgical system if the average pixel classification is below a second contact state threshold lower than the first contact state threshold, that the ultrasound probe is in a second contact state that indicates that the ultrasound probe is not in operative physical contact with the tissue of the patient.

17. The method of claim 16, wherein the local descriptor values characterize at least one of an intensity distribution and a spatial autocorrelation for each pixel in the plurality of pixels.

18. A non-transitory computer-readable medium storing instructions that, when executed, direct a processor of a computing device to:
- control a manipulator arm coupled to an ultrasound probe to position the ultrasound probe within a patient;
- generate an ultrasound image based on sound waves detected by the ultrasound probe while located within the patient;
- determine a plurality of local descriptor values each corresponding to a different pixel included in a plurality of pixels included in the ultrasound image, the plurality of pixels including at least a first pixel corresponding to a first local descriptor value included in the plurality of local descriptor values and a second pixel corresponding to a second local descriptor value included in the plurality of local descriptor values;
- classify each pixel in the plurality of pixels individually as either showing tissue or showing non-tissue, the classifying comprising classifying the first pixel as showing tissue or showing non-tissue based only on the first local descriptor value and classifying the second pixel as showing tissue or showing non-tissue based only on the second local descriptor value;
- determine an average pixel classification representative of a number of pixels included in the plurality of pixels and individually classified as showing tissue compared to a number of pixels included in the plurality of pixels and individually classified as showing non-tissue;
- determine, if the average pixel classification is above a first contact state threshold, that the ultrasound probe is in a first contact state that indicates that the ultrasound probe is in operative physical contact with the tissue of the patient; and
- determine, if the average pixel classification is below a second contact state threshold lower than the first contact state threshold, that the ultrasound probe is in a second contact state that indicates that the ultrasound probe is not in operative physical contact with the tissue of the patient.

* * * * *